US009284358B2

(12) United States Patent
McIntosh et al.

(10) Patent No.: US 9,284,358 B2
(45) Date of Patent: Mar. 15, 2016

(54) CONOTOXIN PEPTIDES

(75) Inventors: J. Michael McIntosh, Salt Lake City, UT (US); Baldomero M. Olivera, Salt Lake City, UT (US); Michael Ellison, Boulder, CO (US); Michelle A. Vincler, Winston-Salem, NC (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 947 days.

(21) Appl. No.: 13/289,494

(22) Filed: Nov. 4, 2011

(65) Prior Publication Data

US 2012/0220539 A1    Aug. 30, 2012

Related U.S. Application Data

(63) Continuation-in-part of application No. 12/307,953, filed as application No. PCT/US2007/016163 on Jul. 17, 2007.

(60) Provisional application No. 60/831,468, filed on Jul. 18, 2006, provisional application No. 61/411,641, filed on Nov. 9, 2010.

(51) Int. Cl.
| *A61K 38/10* | (2006.01) |
| *A61P 25/00* | (2006.01) |
| *C07K 7/08* | (2006.01) |
| *A61P 29/00* | (2006.01) |
| *A61P 35/00* | (2006.01) |
| *C07K 14/435* | (2006.01) |
| *C07K 7/64* | (2006.01) |
| *A61K 38/00* | (2006.01) |

(52) U.S. Cl.
CPC ........... *C07K 14/43504* (2013.01); *A61K 38/00* (2013.01)

(58) Field of Classification Search
None
See application file for complete search history.

(56) References Cited

U.S. PATENT DOCUMENTS

| 6,958,323 | B2 | 10/2005 | Olivera et al. |
| 2003/0109670 | A1 | 6/2003 | Olivera et al. |
| 2005/0215480 | A1 | 9/2005 | Livett et al. |
| 2009/0203616 | A1 | 8/2009 | McIntosh et al. |

FOREIGN PATENT DOCUMENTS

| EP | 1 090 991 A1 | 4/2001 |
| JP | 2002-534996 A | 10/2002 |
| JP | 2003-509045 A | 3/2003 |
| JP | 2005-500017 A | 1/2005 |
| JP | 2009-533355 A | 9/2009 |
| WO | 97/35478 A1 | 10/1997 |
| WO | 00/44769 A1 | 8/2000 |
| WO | 00/44776 A1 | 8/2000 |
| WO | 02/064740 A2 | 8/2002 |
| WO | 02/079236 A1 | 10/2002 |
| WO | WO2008/011006 | * 1/2008 |

OTHER PUBLICATIONS

Lee et al Journal of the National Cancer Institute, Sep. 8, 2010, vol. 102, pp. 1322-1335).*
Werle et al (Amino Acids, 2006, vol. 30, pp. 351-367).*
Johnson D.S. et al., "α-Conotoxin Imi Exhibits Subtype-Specific Nicotinic Acetylcholine Receptor Blockade: Preferential Inhibition of Homomeric α7 and α9 Receptors," Molecular Pharmocology, 48:194-199 (1995).
Vincler et al., PNAS, 2006, vol. 103, pp. 17880-17884.
Satkunanathan, N. et al., "Alpha-conotoxin Vc1.1 Alleviates Neuropathic Pain and Accelerates Functional Recovery of Injured Neurones," Brain Research, 2005, vol. 1059, pp. 149-158.
Lustig, L. "Nicotinic Acetylcholine Receptor Structure and Function in the Efferent Auditory System," The Anatomical Record Part A, Mar. 20, 2006, pp. 424-434, copyright 2006 Wiley-Liss, Inc.
Khalil, Z. et al., "OPL152 ACV1, A Novel Alpha-Conotoxin, Promotes Functional Recovery in Injured Neurons and Reduces Oxidative Stress Levels," Journal of Neurological Sciences, Oral Platform Abstracts, vol. 238, pp. S84-S85, Nov. 10, 2005, Elsevier Scientific Publishing Co., Amsterdam, NL, XP027711165.
McIntosh, J.M. et al., "A Novel α-Conotoxin, PeIA, Cloned from Conus pergrandis, Discriminates Between Rat-α9α10 and α7 Nicotinic Cholinergic Receptors," The Journal of Biological Chemistry, vol. 280, No. 34, Aug. 26, 2005, pp. 30107-30112, copyright 2005 The American Society for Biochemistry and Molecular Biology, Inc.
Ellison, M. et al., "α-Rg1A: A Novel Conotoxin That Specifically and Potentially Blocks the α9α10 nAChR," Biochemistry, vol. 45, No. 5, Feb. 1, 2006, pp. 1511-1517, copyright 2006 American Chemical Society.
Examination Report Feb. 24, 2012 in Australian Application No. 2007275764.
Examination Report dated Apr. 18, 2013 in Australian Application No. 2007275764.
Office Action dated Mar. 26, 2013 in Canadian Application No. 2,657,532.
Office Action mailed Jun. 10, 2015 in U.S. Appl. No. 12/307,953.
Office Action dated May 25, 2015 in Japanese Application No. 2014-11680.
Office Action dated Jul. 18, 2012 in Japanese Application No. 2009-520801.
Office Action dated Aug. 8, 2013 in Japanese Application No. 2009-520801.
Rothlin, et al., "Direct Interaction of Serotonin Type 3 Receptor Ligands with Recombinant and Native Alpha9Alpha10-Containing Nicotinic Cholinergic Receptors," Molecular Pharmacology, vol. 63, No. 5, May 1, 2003, pp. 1067-1074.
Search Report & Written Opinion dated Apr. 9, 2008 in PCT Application No. PCT/US2007/016163.
Search Report dated May 14, 2012 in European Application No. 07796903.

* cited by examiner

*Primary Examiner* — Karen Canella

(57) ABSTRACT

The present invention relates conotoxin peptides that are analogs of the α-conotoxin peptide RgIA. These conotoxin peptides block the α9α10 subtype of the nicotinic acetylcholine receptor (nAChR) and can be used for treating pain, such as neuropathic pain and inflammatory pain, inflammatory disorders, such as rheumatic diseases, and in the treatment of breast cancer.

3 Claims, No Drawings

SEQUENCE LISTING

```
<160> NUMBER OF SEQ ID NOS: 46

<210> SEQ ID NO 1
<211> LENGTH: 13
<212> TYPE: PRT
<213> ORGANISM: Conus regis

<400> SEQUENCE: 1

Gly Cys Cys Ser Asp Pro Arg Cys Arg Tyr Arg Cys Arg
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (1)..(1)
<223> OTHER INFORMATION: Xaa is des-Xaa, pyroglutamic acid, Tyr,
      mono-halo-Tyr, or a fluorescent tag
<220> FEATURE:
<221> NAME/KEY: VARIANT
<222> LOCATION: (3)..(3)
<223> OTHER INFORMATION: Xaa is Cys, selenocysteine, or homocysteine
<220> FEATURE:
<221> NAME/KEY: VARIANT
<222> LOCATION: (5)..(5)
<223> OTHER INFORMATION: Xaa is any amino acid
<220> FEATURE:
<221> NAME/KEY: VARIANT
<222> LOCATION: (9)..(9)
<223> OTHER INFORMATION: Xaa is Cys or selenocysteine
```

-continued

```
<220> FEATURE:
<221> NAME/KEY: VARIANT
<222> LOCATION: (10)..(10)
<223> OTHER INFORMATION: Xaa is Arg, citrulline, omega-nitro-Arg,
      homo-Arg, ornithine, or delta-N-acetyl-ornithine
<220> FEATURE:
<221> NAME/KEY: VARIANT
<222> LOCATION: (11)..(11)
<223> OTHER INFORMATION: Xaa is Tyr, mono-halo-Tyr, Trp, or Phe
<220> FEATURE:
<221> NAME/KEY: VARIANT
<222> LOCATION: (12)..(12)
<223> OTHER INFORMATION: Xaa is Arg, Gln, or His
<220> FEATURE:
<221> NAME/KEY: VARIANT
<222> LOCATION: (14)..(14)
<223> OTHER INFORMATION: Xaa is des-Xaa or any amino acid
<220> FEATURE:
<221> NAME/KEY: VARIANT
<222> LOCATION: (15)..(15)
<223> OTHER INFORMATION: Xaa is des-Xaa, Tyr, mono-halo-Tyr, or a
      fluorescent tag

<400> SEQUENCE: 2

Xaa Gly Xaa Cys Xaa Asp Pro Arg Xaa Xaa Xaa Xaa Cys Xaa Xaa
1               5                   10                  15

<210> SEQ ID NO 3
<211> LENGTH: 13
<212> TYPE: PRT
<213> ORGANISM: Artificial Sequence
<220> FEATURE:
<223> OTHER INFORMATION: Analog of Conus regis RgIA

<400> SEQUENCE: 3

Gly Cys Cys Thr Asp Pro Arg Cys Arg Tyr Arg Cys Arg
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (6)..(6)
<223> OTHER INFORMATION: Xaa is hydroxy-Pro

<400> SEQUENCE: 4

Gly Cys Cys Ser Asp Xaa Arg Cys Arg Tyr Arg Cys Arg
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (10)..(10)
<223> OTHER INFORMATION: Xaa is mono-halo-Tyr

<400> SEQUENCE: 5

Gly Cys Cys Ser Asp Pro Arg Cys Arg Xaa Arg Cys Arg
1               5                   10

<210> SEQ ID NO 6
<211> LENGTH: 13
<212> TYPE: PRT
```

```
<213> ORGANISM: Artificial Sequence
<220> FEATURE:
<223> OTHER INFORMATION: Analog of Conus regis RgIA
<220> FEAT

```
1               5                   10
```

<210> SEQ ID NO 11
<211> LENGTH: 13
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (9)..(9)
<223> OTHER INFORMATION: Xaa is homo-Arg

<400> SEQUENCE: 11

```
Gly Cys Cys Ser Asp Pro Arg Cys Xaa Tyr Arg Cys Arg
1               5                   10
```

<210> SEQ ID NO 12
<211> LENGTH: 13
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (9)..(9)
<223> OTHER INFORMATION: Xaa is ornithine

<400> SEQUENCE: 12

```
Gly Cys Cys Ser Asp Pro Arg Cys Xaa Tyr Arg Cys Arg
1               5                   10
```

<210> SEQ ID NO 13
<211> LENGTH: 13
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (9)..(9)
<223> OTHER INFORMATION: Xaa is delta-N-acetyl-ornithine

<400> SEQUENCE: 13

```
Gly Cys Cys Ser Asp Pro Arg Cys Xaa Tyr Arg Cys Arg
1               5                   10
```

<210> SEQ ID NO 14
<211> LENGTH: 13
<212> TYPE: PRT
<213> ORGANISM: Artificial Sequence
<220> FEATURE:
<223> OTHER INFORMATION: Analog of Conus regis RgIA

<400> SEQUENCE: 14

```
Gly Cys Cys Ser Asp Pro Arg Cys Lys Tyr Arg Cys Arg
1               5                   10
```

<210> SEQ ID NO 15
<211> LENGTH: 13
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (10)..(10)
<223> OTHER INFORMATION: Xaa is iodo-Tyr

<400> SEQUENCE: 15

```
Gly Cys Cys Ser Asp Pro Arg Cys Arg Xaa Arg Cys Arg
1               5                   10
```

<210> SEQ ID NO 16
<211> LENGTH: 13
<212> TYPE: PRT
<213> ORGANISM: Artificial Sequence
<220> FEATURE:
<223> OTHER INFORMATION: Analog of Conus regis RgIA

<400> SEQUENCE: 16

```
Gly Cys Cys Ser Asp Pro Arg Cys Arg Trp Arg Cys Arg
1               5                   10
```

<210> SEQ ID NO 17
<211> LENGTH: 13
<212> TYPE: PRT
<213> ORGANISM: Artificial Sequence
<220> FEATURE:
<223> OTHER INFORMATION: Analog of Conus regis RgIA

<400> SEQUENCE: 17

```
Gly Cys Cys Ser Asp Pro Arg Cys Arg Phe Arg Cys Arg
1               5                   10
```

<210> SEQ ID NO 18
<211> LENGTH: 13
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (9)..(9)
<223> OTHER INFORMATION: Xaa is citrulline
<220> FEATURE:
<221> NAME/KEY: VARIANT
<222> LOCATION: (10)..(10)
<223> OTHER INFORMATION: Xaa is iodo-Tyr

<400> SEQUENCE: 18

```
Gly Cys Cys Ser Asp Pro Arg Cys Xaa Xaa Arg Cys Arg
1               5                   10
```

<210> SEQ ID NO 19
<211> LENGTH: 13
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (9)..(9)
<223> OTHER INFORMATION: Xaa is omega-nitro-Arg
<220> FEATURE:
<221> NAME/KEY: VARIANT
<222> LOCATION: (10)..(10)
<223> OTHER INFORMATION: Xaa is iodo-Tyr

<400> SEQUENCE: 19

```
Gly Cys Cys Ser Asp Pro Arg Cys Xaa Xaa Arg Cys Arg
1               5                   10
```

<210> SEQ ID NO 20
<211> LENGTH: 13
<212> TYPE: PRT
<213> ORGANISM: Artificial Sequence
<220> FEATURE:
<223> OTHER INFORMATION: Analog of Conus regis RgIA

<400> SEQUENCE: 20

Gly Cys Cys Ala Asp Pro Arg Cys Arg Tyr Arg Cys Arg
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: MOD_RES
<222> LOCATION: (12)..(12)
<223> OTHER INFORMATION: AMIDATION

<400> SEQUENCE: 21

Gly Cys Cys Ser Asp Pro Arg Cys Arg Tyr Arg Cys
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Analog of Conus regis RgIA

<400> SEQUENCE: 22

Gly Cys Cys Ser Glu Pro Arg Cys Arg Tyr Arg Cys Arg
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Analog of Conus regis RgIA

<400> SEQUENCE: 23

Gly Cys Cys Ser Asp Val Arg Cys Arg Tyr Arg Cys Arg
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Analog of Conus regis RgIA

<400> SEQUENCE: 24

Gly Cys Cys Ser Asp Pro Arg Cys Ala Tyr Arg Cys Arg
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Analog of Conus regis RgIA

<400> SEQUENCE: 25

Gly Cys Cys Ser His Pro Ala Cys Arg Tyr Arg Cys Arg
1               5                   10

<210> SEQ ID NO 26
<211> LENGTH: 13
<212> TYPE: PRT

```
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (9)..(9)
<223> OTHER INFORMATION: Xaa is D-Arg

<400> SEQUENCE: 26

Gly Cys Cys Ser Asp Pro Arg Cys Xaa Tyr Arg C

```
<221> NAME/KEY: VARIANT
<222> LOCATION: (9)..(9)
<223> OTHER INFORMATION: Xaa is citrulline
<220> FEATURE:
<221> NAME/KEY: VARIANT
<222> LOCATION: (10)..(10)
<223> OTHER INFORMATION: Xaa is mono-iodo-Tyr

<400> SEQUENCE: 29

Gly Xaa Cys Thr Asp Pro Arg Xaa Xaa Xaa Gln Cys Leu
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (2)..(2)
<223> OTHER INFORMATION: Xaa is selenocysteine
<220> FEATURE:
<221> NAME/KEY: VARIANT
<222> LOCATION: (8)..(8)
<223> OTHER INFORMATION: Xaa is selenocysteine

<400> SEQUENCE: 30

Gly Xaa Cys Ser Asp Pro Arg Xaa Arg Tyr Arg Cys Arg
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (9)..(9)
<223> OTHER INFORMATION: Xaa is citrulline
<220> FEATURE:
<221> NAME/KEY: VARIANT
<222> LOCATION: (10)..(10)
<223> OTHER INFORMATION: Xaa is mono-iodo-Tyr

<400> SEQUENCE: 31

Gly Cys Cys Thr Asp Pro Arg Cys Xaa Xaa Arg Cys Arg
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Analog of Conus regis RgIA

<400> SEQUENCE: 32

Gly Cys Cys Ser Asp Pro Arg Cys Arg Tyr Gln Cys Arg
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (2)..(2)
<223> OTHER INFORMATION: Xaa is homocysteine
```

```
<400> SEQUENCE: 33

Gly Xaa Cys Ser Asp Pro Arg Cys Arg Tyr Arg Cys Arg
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Analog of Conus regis RgIA

<400> SEQUENCE: 34

Gly Cys Cys Tyr Asp Pro Arg Cys Arg Tyr Arg Cys Arg
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (8)..(8)
<223> OTHER INFORMATION: Xaa is homocysteine

<400> SEQUENCE: 35

Gly Cys Cys Ser Asp Pro Arg Xaa Arg Tyr Arg Cys Arg
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Analog of Conus regis RgIA

<400> SEQUENCE: 36

Gly Cys Cys Ser Asp Pro Arg Cys Arg Tyr His Cys Arg
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (6)..(6)
<223> OTHER INFORMATION: Xaa is hydroxy-Pro

<400> SEQUENCE: 37

Gly Cys Cys Thr Asp Xaa Arg Cys Arg Tyr Arg Cys Arg
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (10)..(10)
<223> OTHER INFORMATION: Xaa is mono-halo-Tyr

<400> SEQUENCE: 38
```

```
Gly Cys Cys Thr Asp Pro Arg Cys Arg Xaa Arg Cys Arg
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (6)..(6)
<223> OTHER INFORMATION: Xaa is hydroxy-Pro
<220> FEATURE:
<221> NAME/KEY: VARIANT
<222> LOCATION: (10)..(10)
<223> OTHER INFORMATION: Xaa is mono-halo-Tyr

<400> SEQUENCE: 39

Gly Cys Cys Thr Asp Xaa Arg Cys Arg Xaa Arg Cys Arg
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Analog of Conus regis RgIA

<400> SEQUENCE: 40

Gly Cys Cys Ser Asp Pro Arg Cys Phe Trp Arg Cys Arg
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (10)..(10)
<223> OTHER INFORMATION: Xaa is mono-iodo-Tyr

<400> SEQUENCE: 41

Gly Cys Cys Ser Asp Pro Arg Cys Arg Xaa Arg Cys Arg
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (9)..(9)
<223> OTHER INFORMATION: Xaa is citrulline
<220> FEATURE:
<221> NAME/KEY: VARIANT
<222> LOCATION: (10)..(10)
<223> OTHER INFORMATION: Xaa is iodo-Tyr

<400> SEQUENCE: 42

Gly Cys Cys Thr Asp Pro Arg Cys Xaa Xaa Gln Cys Arg
1               5                   10

<210> SEQ ID NO 43
<211> LENGTH: 13
```

```
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (9)..(9)
<223> OTHER INFORMATION: Xaa is citrulline
<220> FEATURE:
<221> NAME/KEY: VARIANT
<222> LOCATION: (10)..(10)
<223> OTHER INFORMATION: Xaa is mono-iodo-Tyr

<400> SEQUENCE: 43

Gly Cys Cys Ser Asp Pro Arg Cys Xaa Xaa Arg Cys Arg
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (2)..(2)
<223> OTHER INFORMATION: Xaa is selenocysteine
<220> FEATURE:
<221> NAME/KEY: VARIANT
<222> LOCATION: (8)..(8)
<223> OTHER INFORMATION: Xaa is selenocysteine
<220> FEATURE:
<221> NAME/KEY: VARIANT
<222> LOCATION: (9)..(9)
<223> OTHER INFORMATION: Xaa is citrulline
<220> FEATURE:
<221> NAME/KEY: VARIANT
<222> LOCATION: (10)..(10)
<223> OTHER INFORMATION: Xaa is iodo-Tyr

<400> SEQUENCE: 44

Gly Xaa Cys Thr Asp Pro Arg Xaa Xaa Xaa Gln Cys Arg
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (2)..(2)
<223> OTHER INFORMATION: Xaa is selenocysteine
<220> FEATURE:
<221> NAME/KEY: VARIANT
<222> LOCATION: (8)..(8)
<223> OTHER INFORMATION: Xaa is selenocysteine
<220> FEATURE:
<221> NAME/KEY: VARIANT
<222> LOCATION: (9)..(9)
<223> OTHER INFORMATION: Xaa is citrulline
<220> FEATURE:
<221> NAME/KEY: VARIANT
<222> LOCATION: (10)..(10)
<223> OTHER INFORMATION: Xaa is iodo-Tyr

<400> SEQUENCE: 45

Gly Xaa Cys Thr Asp Pro Arg Xaa Xaa Xaa Gln Cys Leu
1               5                   10

<210> SEQ ID NO 46
<211> LENGTH: 13
```

```
<212> TYPE: PRT
<213> ORGANISM: Artificial Sequence
<220> FEATURE:
<223> OTHER INFORMATION: Analog of Conus regis RgIA
<220> FEATURE:
<221> NAME/KEY: VARIANT
<222> LOCATION: (9)..(9)
<223> OTHER INFORMATION: Xaa is citrulline
<220> FEATURE:
<221> NAME/KEY: VARIANT
<222> LOCATION: (10)..(10)
<223> OTHER INFORMATION: Xaa is iodo-Tyr

<400> SEQUENCE: 46

Gly Cys Cys Thr Asp Pro Arg Cys Xaa Xaa Arg Cys Arg
1               5                   10
```

CONOTOXIN PEPTIDES

CROSS-REFERENCE TO RELATED APPLICATION

The present application is a continuation-in-part of U.S. patent application Ser. No. 12/307,953 filed 24 Apr. 2009, which is a national stage filing under 35 U.S.C. §371 of PCT/US2007/016163, filed on 17 Jul. 2007 which in turn is related to and claims priority under 35 U.S.C. §119(e) to U.S. provisional patent application Ser. No. 60/831,468 filed on 18 Jul. 2006. The present application is related to and claims priority under 35 U.S.C. §119(e) to U.S. provisional patent application Ser. No. 61/411,641 filed on 9 Nov. 2010. Each application is incorporated herein by reference.

REFERENCE TO GOVERNMENT SUPPORT

This invention was made with Government support under Grant Nos. MH 53631, GM48677 and NS048158 awarded by the National Institutes of Health, Bethesda, Md. The United States Government has certain rights in the invention.

SEQUENCE SUBMISSION

The present application is being filed along with a Sequence Listing in electronic format. The Sequence Listing is entitled 2323247NPSequenceListing.txt, created on 5 Oct. 2011 and is 13 kb in size. The information in the electronic format of the Sequence Listing is part of the present application and is incorporated herein by reference in its entirety.

BACKGROUND OF THE INVENTION

The present invention relates conotoxin peptides that are analogs of the α- teine (sel), X5 is Arg, citrulline, ω-nitro-Arg, homo-Arg, ornithine or δ-N-acetyl-ornithine, X6 is Tyr, mono-halo-Tyr, Trp or Phe, X7 is Arg, Gln or His, X8 is des-X8 or any amino acid, and X9 is des-X9, Tyr, mono-halo-Tyr or a fluorescent tag; with the proviso that the conotoxin peptide is not a peptide defined below. In some embodiments X3 is Ser, Thr, Ala, Tyr, halo-Tyr, Asn, Ile or Arg. In other embodiments, X8 is Leu, Glu, Gln or Lys. In some embodiments, Gly can be replaced with pyroglutamic acid, Tyr, mono-halo-Tyr or a fluorescent tag. In further embodiments, X8 can be replaced with Tyr, mono-halo-Tyr or a fluorescent tag. In other embodiments, when X8 is des-X8 and X9 is des-X9, the N-terminal Cys is an amide. In further embodiments, Asp can be replaced with Asn or Glu. In some embodiments, Pro can be replaced with hydroxy-Pro. In other embodiments, the Cys residues can be substituted by selenocysteines. In further embodiments, halo is iodine or bromine. In accordance with the proviso for the present invention, the conotoxin peptide of SEQ ID NO:2 is not a conotoxin peptide having the following formulas:

GCCSDPRCRYRCR (SEQ ID NO:1);
GCCTDPRCRYRCR (SEQ ID NO:3);
GCCSDX1RCRYRCR (SEQ ID NO:4), where X1 is hydroxy-Pro;
GCCTDX1RCRYRCR (SEQ ID NO:37), where X1 is hydroxy-Pro;
GCCSDPRCRX1RCR (SEQ ID NO:5), where X1 is mono-halo Tyr, such as iodo-Tyr or bromo-Tyr;
GCCTDPRCRX1RCR (SEQ ID NO:38), where X1 is mono-halo Tyr, such as iodo-Tyr or bromo-Tyr;
GCCSDX1RCRX2RCR (SEQ ID NO:6)), where X1 is hydroxy-Pro and X2 is mono-halo Tyr, such as iodo-Tyr or bromo-Tyr;
GCCTDX1RCRX2RCR (SEQ ID NO:39)), where X1 is hydroxy-Pro and X2 is mono-halo Tyr, such as iodo-Tyr or bromo-Tyr;
GCCSDPRCX1YRCR (SEQ ID NO:7), where X1 is homo-Arg or ornithine;
GCCSDPRCRYRCK (SEQ ID NO:8); and
any peptide specifically disclosed in U.S. Pat. No. 7,279,549.

The present invention also relates to the specific RgIA analogs as set forth in Tables 1 and 2 below or such analogs further modified by (i) additions made to the C-terminus, such as Tyr, iodo-Tyr, a fluorescent tag or (ii) additions made to the N-terminus, such as Tyr, iodo-Tyr, pyroglutamate or a fluorescent tag. Additional analogs include any combination of the substituted amino acid residues shown in Tables 1 and 2.

In addition, residues or groups of residues known to the skilled artisan to improve stability can be added to the C-terminus and/or N-terminus. Also, residues or groups of residues known to the skilled artisan to improve oral availability can be added to the C-terminus and/or N-terminus. In addition, the above residues or groups that can be added to the C-terminus can also replace X8 in SEQ ID NO:2. Finally, the above residues or groups that can be added to the N-terminus can also replace the Gly in SEQ ID NO:2.

The present invention is further directed to derivatives of the above peptides which are acylic permutations in which the cyclic permutants retain the native bridging pattern of native conotoxin peptide (Craik et al. (2001), e.g., a cyclized conotoxin peptide having an amide cyclized backbone such that the conotoxin peptide has no free N- or C-terminus in which the conotoxin peptide comprises the native disulfide bonds (U.S. Pat. No. 7,312,195). In one embodiment, the cyclized conotoxin peptide comprises a linear conotoxin peptide and a peptide linker, wherein the N- and C-termini of the linear conotoxin peptide are linked via the peptide linker to form the amide cyclized peptide backbone. In some embodiments, the peptide linker comprises amino acids selected from the group consisting of glycine, alanine and combinations thereof.

In a second aspect, the conotoxin peptides of the present invention which block the α9α10 subtype of the nAChR are useful in treating pain, including chronic pain, neuropathic pain and inflammatory pain, and other inflammatory conditions or disorders.

In a third aspect, the conotoxin peptides of the present invention which block the α9α10 subtype of the nAChR are useful for inhibiting the migration of immune cells, for treating inflammatory conditions or disorders and for reducing inflammation such as associated with rheumatic diseases.

In a fourth aspect, the conotoxin peptides of the present invention which block the α9 containing subtypes of the nAChR are useful in the treatment of treating breast cancer.

DETAILED DESCRIPTION OF THE INVENTION

The present invention relates conotoxin peptides that are analogs of the α-conotoxin peptide RgIA. These conotoxin peptides block the α9α10 subtype of the nicotinic acetylcholine receptor (nAChR) and can be used for treating pain, including neuropathic pain and inflammatory pain, for inhibiting migration of immune cells, for treating inflammatory disorders, for reducing inflammation associated with disorders such as rheumatic diseases and in the treatment of breast cancer.

The activity of certain α-conotoxins, including RgIA, in blocking the α9α10 subtype of the nAChR has been shown herein in studies using oocytes that express different subtypes of the nAChR (Ellison et al., 2006; Vincler et al., 2006; WO 2008/011006; US 2009/0203616). The activity of α-conotoxins, including RgIA, as an antinocieceptive and an analgesic has been shown in studies of chronic constriction injury (Vincler et al., 2006; WO 2008/011006; US 2009/0203616). The activity of α-conotoxins, including RgIA, in inhibiting migration of immune cells has been shown in studies of chronic constriction injury (Vincler et al., 2006; WO 2008/011006; US 2009/0203616). Compounds that block the α9α10 nAChR or α9 containing nAChRs are useful as analgesic agents, as agents for inhibiting the migration of immune cells, as agents for treating inflammatory pain and other inflammatory conditions or disorders, as agents for reducing inflammation associated with disorders such as rheumatic diseases and as agents in the treatment of breast cancer. Inflammatory conditions include, but are not limited to, sepsis, fibromyalgia, inflammatory bowel disease (including, but not limited to ulcerative colitis and Crohn's disease), sarcoidosis, endometriosis, uterine fibroids, inflammatory skin diseases including but not limited to psoriasis, impaired wound healing, inflammatory conditions of the lungs including, but not limited to asthma and chronic obstructive pulmonary disease, diseases associated with inflammation of the nervous system including Parkinson's Disease and Alzheimer's Disease, periodontal disease, and cardiovascular disease. Rheumatic diseases include, but are not limited to, arthritis, lupus, ankylosing spondylitis, fibromyalgia, tendonitis, bursitis, scleroderma, and gout.

Thus, the present invention relates to conotoxin peptides that are analogs of the α-conotoxin peptide RgIA. The conotoxin peptides of the present invention have the formula X1GX2CX3DPRX4X5X6X7CX8X9 (SEQ ID NO:2), wherein X1 is des-X1, pyroglutamic acid, Tyr, mono-halo-Tyr or a fluorescent tag, X2 is Cys, selenocysteine (sel) or homocysteine, X3 is any amino acid, X4 is Cys or selenocysteine (sel), X5 is Arg, citrulline, ω-nitro-Arg, homo-Arg, ornithine or δ-N-acetyl-ornithine, X6 is Tyr, mono-halo-Tyr, Trp or Phe, X7 is Arg, Gln or His, X8 is des-X8 or any amino acid, and X9 is des-X9, Tyr, mono-halo-Tyr or a fluorescent tag; with the proviso that the conotoxin peptide is not peptide defined below. In some embodiments X3 is Ser, Thr, Ala, Tyr, halo-Tyr, Asn, Ile or Arg. In other embodiments, X8 is Leu, Glu, Gln or Lys. In some embodiments, Gly can be replaced with pyroglutamic acid, Tyr, mono-halo-Tyr or a fluorescent tag. In further embodiments, X8 can be replaced with Tyr, mono-halo-Tyr or a fluorescent tag. In other embodiments, when X8 is des-X8 and X9 is des-X9, the N-terminal Cys is an amide. In further embodiments, Asp can be replaced with Asn. In some embodiments, Pro can be replaced with hydroxy-Pro. In other embodiments, the Cys residues can be substituted by selenocysteines. In further embodiments, halo is iodine or bromine. In accordance with the proviso for the present invention, the conotoxin peptide of SEQ ID NO:2 is not a conotoxin peptide having the following formulas:

GCCSDPRCRYRCR (SEQ ID NO:1);
GCCTDPRCRYRCR (SEQ ID NO:3);
GCCSDX1RCRYRCR (SEQ ID NO:4), where X1 is hydroxy-Pro;
GCCSDPRCRX1RCR (SEQ ID NO:5), where X1 is mono-halo Tyr, such as iodo-Tyr or bromo-Tyr;
GCCSDX1RCRX2RCR (SEQ ID NO:6)), where X1 is hydroxy-Pro and X2 is mono-halo Tyr, such as iodo-Tyr or bromo-Tyr;
GCCSDPRCX1YRCR (SEQ ID NO:7), where X1 is homo-Arg or ornithine;
GCCSDPRCRYRCX1 (SEQ ID NO:8), where X1 is Lys; and
any peptide specifically disclosed in U.S. Pat. No. 7,279, 549.

The present invention also relates to the specific RgIA analogs as set forth in Tables 1 and 2 below or such analogs further modified by (i) additions made to the C-terminus, such as Tyr, iodo-Tyr, a fluorescent tag or (ii) additions made to the N-terminus, such as Tyr, iodo-Tyr, pyroglutamate or a fluorescent tag. Additional analogs include any combination of the substituted amino acid residues shown in Tables 1 and 2.

In addition, residues or groups of residues known to the skilled artisan to improve stability can be added to the C-terminus and/or N-terminus. Also, residues or groups of residues known to the skilled artisan to improve oral availability can be added to the C-terminus and/or N-terminus. In addition, the above residues or groups that can be added to the C-terminus can also replace X8 in SEQ ID NO:2. Finally, the above residues or groups that can be added to the N-terminus can also replace the Gly in SEQ ID NO:2.

The present invention is further directed to derivatives of the above peptides which are acylic permutations in which the cyclic permutants retain the native bridging pattern of native conotoxin peptide (Craik et al. (2001), e.g., a cyclized conotoxin peptide having an amide cyclized backbone such that the conotoxin peptide has no free N- or C-terminus in which the conotoxin peptide comprises the native disulfide bonds (U.S. Pat. No. 7,312,195). In one embodiment, the cyclized conotoxin peptide comprises a linear conotoxin peptide and a peptide linker, wherein the N- and C-termini of the linear conotoxin peptide are linked via the peptide linker to form the amide cyclized peptide backbone. In some embodiments, the peptide linker comprises amino acids selected from the group consisting of glycine, alanine and combinations thereof.

The conotoxin peptides of the present invention are useful in methods of treating or preventing conditions or disorders associated with the α9α10 subtype or α9 containing subtypes of the nicotinic acetylcholine receptor (nAChR) in an individual. Such methods comprise administering to an individual in need thereof a therapeutically effective amount of an active agent or a pharmaceutically acceptable salt thereof, wherein the active agent blocks the α9α10 subtype of the nAChR. In one embodiment, the condition is pain and the administration of the active agent alleviates pain in the individual. In a second embodiment, the condition is inflammation mediated by immune cells and the administration of the active agent reduces inflammation. In one embodiment, the inflammation is associated with rheumatic diseases. In a third embodiment, the condition is breast cancer.

The conotoxin peptides of the present invention are useful in methods of inhibiting migration of immune cells in an individual in need thereof. Such methods comprise administering to an individual an immune cell migration-inhibiting amount of an active agent or a pharmaceutically acceptable salt thereof, wherein said active agent blocks the α9α10 subtype of the nicotinic acetylcholine receptor (nAChR).

The conotoxin peptides of the present invention are useful in methods of identifying drug candidates for use as treating or preventing conditions or disorders associated with the α9α10 subtype or α9 containing subtypes of the nicotinic acetylcholine receptor (nAChR) or for inhibiting the migration immune cells which comprises screening a drug candidate for its ability to block the activity of the α9α10 subtype of the nAChR. In one embodiment, the displacement of a labeled conotoxin peptide of the present invention from the α9α10 subtype of the nAChR by a candidate drug agent is used to identify suitable candidate drugs. In a second embodiment, a biological assay on a drug candidate to determine the therapeutic activity is conducted and compared to the results obtained from the biological assay of a conotoxin peptide of the present invention. In a third embodiment, the binding affinity of a drug candidate to the α9α10 subtype of the nAChR is measured and compared to the binding affinity of a conotoxin peptide of the present invention to the α9α10 subtype of the nAChR. In a fourth embodiment, the effect of a drug candidate on the function of the α9α10 subtype of the nAChR is analyzed by measuring the effect in functional assays, such as electrophysiological assays, calcium imaging assays and the like. These latter assays can measure the ability of the drug candidate to block the function of α9 homomers and/or α9α10 heteromers.

The conotoxin peptides of the present invention are useful in methods of identifying compounds that mimic the therapeutic activity of a conotoxin peptide of the present invention. Such methods comprise the steps of: (a) conducting a biological assay on a test compound to determine the therapeutic activity; and (b) comparing the results obtained from the biological assay of the test compound to the results obtained from the biological assay of a conotoxin peptides of the present invention.

Thus, the present invention also relates to rational drug design for the identification of additional drugs which can be used for the purposes described herein. The goal of rational drug design is to produce structural analogs of biologically active polypeptides of interest or of small molecules that also act on the receptor (e.g., agonists, antagonists, inhibitors) in order to fashion drugs which are, for example, more active or stable forms of the polypeptide, or which, e.g., enhance or interfere with the function of a polypeptide in vivo. Several approaches for use in rational drug design include analysis of three-dimensional structure, alanine scans, molecular modeling and use of anti-id antibodies. These techniques are well known to those skilled in the art. Such techniques may include providing atomic coordinates defining a three-dimensional structure of a protein complex formed by said first polypeptide and said second polypeptide, and designing or selecting compounds capable of interfering with the interaction between a first polypeptide and a second polypeptide based on said atomic coordinates.

Following identification of a substance which modulates or affects polypeptide activity, the substance may be further investigated. Furthermore, it may be manufactured and/or used in preparation, i.e., manufacture or formulation, or a composition such as a medicament, pharmaceutical composition or drug. These may be administered to individuals.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This approach might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

A template molecule is then selected, onto which chemical groups that mimic the pharmacophore can be grafted. The template molecule and the chemical groups grafted thereon can be conveniently selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent it is exhibited. Further optimization or modification can then be carried out to arrive at one or more final mimetics for in vivo or clinical testing.

The present invention further relates to the use of a labeled (e.g., radiolabel, fluorophore, chromophore or the like) of the conotoxins described herein as a molecular tool both in vitro and in vivo, for discovery of small molecules that exert their action at or partially at the same functional site as the native toxin and capable of elucidation similar functional responses as the native toxin. In one embodiment, the displacement of a labeled conotoxin from its receptor, i.e., $\alpha 9\alpha 10$ nAChR, or other complex by a candidate drug agent is used to identify suitable candidate drugs. In a second embodiment, a biological assay on a test compound to determine the therapeutic activity is conducted and compared to the results obtained from the biological assay of a conotoxin. In a third embodiment, the binding affinity of a small molecule to the receptor of a conotoxin, i.e., $\alpha 9\alpha 10$ nAChR, is measured and compared to the binding affinity of a conotoxin to its receptor, i.e., $\alpha 9\alpha 10$ nAChR. In a fourth embodiment, the effect of a drug candidate on the function of the $\alpha 9\alpha 10$ subtype of the nAChR is analyzed by measuring the effect in functional assays, such as electrophysiological assays, calcium imaging assays and the like. In this manner, candidate drugs are identified that block the $\alpha 9\alpha 10$ nAChR and are useful as analgesic agents, as agents for inhibiting the migration of immune cells, as agents for treating inflammatory pain and other inflammatory disorders and as agents for reducing inflammation, such as inflammation associated with arthritis.

Pharmaceutical compositions containing a compound of the present invention as the active ingredient can be prepared according to conventional pharmaceutical compounding techniques. See, for example, *Remington: The Science and Practice of Pharmacy,* 21st Ed., Lippincott Williams & Wilkins, Philadelphia, 2005. Typically, an antagonistic amount of active ingredient will be admixed with a pharmaceutically acceptable carrier. The carrier may take a wide variety of forms depending on the form of preparation desired for administration, e.g., intravenous, oral, parenteral or intrathecally. For examples of delivery methods see U.S. Pat. No. 5,844,077, incorporated herein by reference.

"Pharmaceutical composition" means physically discrete coherent portions suitable for medical administration. "Pharmaceutical composition in dosage unit form" means physically discrete coherent units suitable for medical administration, each containing a daily dose or a multiple (up to four times) or a sub-multiple (down to a fortieth) of a daily dose of the active compound in association with a carrier and/or enclosed within an envelope. Whether the composition contains a daily dose, or for example, a half, a third or a quarter of a daily dose, will depend on whether the pharmaceutical composition is to be administered once or, for example, twice, three times or four times a day, respectively.

The term "salt", as used herein, denotes acidic and/or basic salts, formed with inorganic or organic acids and/or bases, preferably basic salts. While pharmaceutically acceptable salts are preferred, particularly when employing the compounds of the invention as medicaments, other salts find utility, for example, in processing these compounds, or where non-medicament-type uses are contemplated. Salts of these compounds may be prepared by art-recognized techniques.

Examples of such pharmaceutically acceptable salts include, but are not limited to, inorganic and organic addition salts, such as hydrochloride, sulphates, nitrates or phosphates and acetates, trifluoroacetates, propionates, succinates, benzoates, citrates, tartrates, fumarates, maleates, methane-sulfonates, isothionates, theophylline acetates, salicylates, respectively, or the like. Lower alkyl quaternary ammonium salts and the like are suitable, as well.

As used herein, the term "pharmaceutically acceptable" carrier means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution;

ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, aloha-tocopherol and the like; and the metal chelating agents such as citric acid, ethylenediamine tetraacetic acid (EDTA), sorbitol, tartaric acid, phosphoric acid and the like.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

A variety of administration routes are available. The particular mode selected will depend of course, upon the particular drug selected, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal or parenteral routes. The term "parenteral" includes subcutaneous, intravenous, epidural, irrigation, intramuscular, release pumps, or infusion.

For example, administration of the active agent according to this invention may be achieved using any suitable delivery means, including:

(a) pump (see, e.g., Luer and Hatton (1993), Zimm et al. (1984) and Ettinger et al. (1978));

(b), microencapsulation (see, e.g., U.S. Pat. Nos. 4,352,883; 4,353,888; and 5,084,350);

(c) continuous release polymer implants (see, e.g., U.S. Pat. No. 4,883,666);

(d) macroencapsulation (see, e.g., U.S. Pat. Nos. 5,284,761, 5,158,881, 4,976,859 and 4,968,733 and published PCT patent applications WO92/19195, WO 95/05452);

(e) naked or unencapsulated cell grafts to the CNS (see, e.g., U.S. Pat. Nos. 5,082,670 and 5,618,531);

(f) injection, either subcutaneously, intravenously, intraarterially, intramuscularly, or to other suitable site; or (g) oral administration, in capsule, liquid, tablet, pill, or prolonged release formulation.

In one embodiment of this invention, an active agent is delivered directly into the CNS, preferably to the brain ventricles, brain parenchyma, the intrathecal space or other suitable CNS location, most preferably intrathecally.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Active agents, which may be peptides, can also be administered in a cell based delivery system in which a DNA sequence encoding an active agent is introduced into cells designed for implantation in the body of the patient, especially in the spinal cord region. Suitable delivery systems are described in U.S. Pat. No. 5,550,050 and published PCT Application Nos. WO 92/19195, WO 94/25503, WO 95/01203, WO 95/05452, WO 96/02286, WO 96/02646, WO 96/40871, WO 96/40959 and WO 97/12635. Suitable DNA sequences can be prepared synthetically for each active agent on the basis of the developed sequences and the known genetic code.

The active agent is preferably administered in a therapeutically effective amount. By a "therapeutically effective amount" or simply "effective amount" of an active compound is meant a sufficient amount of the compound to treat the desired condition at a reasonable benefit/risk ratio applicable to any medical treatment. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington: The Science and Practice of Pharmacy.*

Dosage may be adjusted appropriately to achieve desired drug levels, locally or systemically. Typically the active agents of the present invention exhibit their effect at a dosage range from about 0.001 mg/kg to about 250 mg/kg, preferably from about 0.01 mg/kg to about 100 mg/kg of the active ingredient, more preferably from a bout 0.05 mg/kg to about 75 mg/kg. A suitable dose can be administered in multiple sub-doses per day. Typically, a dose or sub-dose may contain from about 0.1 mg to about 500 mg of the active ingredient per unit dosage form. A more preferred dosage will contain from about 0.5 mg to about 100 mg of active ingredient per unit dosage form. Dosages are generally initiated at lower levels and increased until desired effects are achieved. In the event that the response in a subject is insufficient at such doses, even higher doses (or effective higher doses by a different, more localized delivery route) may be employed to the extent that patient tolerance permits. Continuous dosing over, for example, 24 hours or multiple doses per day are contemplated to achieve appropriate systemic levels of compounds.

Advantageously, the compositions are formulated as dosage units, each unit being adapted to supply a fixed dose of active ingredients. Tablets, coated tablets, capsules, ampoules and suppositories are examples of dosage forms according to the invention.

It is only necessary that the active ingredient constitute an effective amount, i.e., such that a suitable effective dosage will be consistent with the dosage form employed in single or multiple unit doses. The exact individual dosages, as well as daily dosages, are determined according to standard medical principles under the direction of a physician or veterinarian for use humans or animals.

The pharmaceutical compositions will generally contain from about 0.0001 to 99 wt. %, preferably about 0.001 to 50 wt. %, more preferably about 0.01 to 10 wt. % of the active ingredient by weight of the total composition. In addition to the active agent, the pharmaceutical compositions and medicaments can also contain other pharmaceutically active compounds. Examples of other pharmaceutically active compounds include, but are not limited to, analgesic agents, cytokines and therapeutic agents in all of the major areas of clinical medicine. When used with other pharmaceutically active compounds, the active agents of the present invention may be delivered in the form of drug cocktails. A cocktail is a mixture of any one of the compounds useful with this invention with another drug or agent. In this embodiment, a common administration vehicle (e.g., pill, tablet, implant, pump, injectable solution, etc.) would contain both the instant composition in combination with a supplementary potentiating agent. The individual drugs of the cocktail are each administered in therapeutically effective amounts. A therapeutically effective amount will be determined by the parameters described above; but, in any event, is that amount which establishes a level of the drugs in the area of body where the drugs are required for a period of time which is effective in attaining the desired effects.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., *Molecular Cloning* (Cold Spring Harbor Laboratory Press, Cold Spring Harbor, N.Y., 1982); Sambrook et al., *Molecular Cloning*, 2nd Ed. (Cold Spring Harbor Laboratory Press, Cold Spring Harbor, N.Y., 1989); Sambrook and Russell, *Molecular Cloning*, 3rd Ed. (Cold Spring Harbor Laboratory Press, Cold Spring Harbor, N.Y., 2001); Ausubel et al., *Current Protocols in Molecular Biology* (John Wiley & Sons, updated through 2005); Glover, *DNA Cloning* (IRL Press, Oxford, 1985); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, *Antibodies*, (Cold Spring Harbor Laboratory Press, Cold Spring Harbor, N.Y., 1998); Jakoby and Pastan, 1979; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, (Blackwell Scientific Publications, Oxford, 1988); Hogan et al., *Manipulating the Mouse Embryo*, (Cold Spring Harbor Laboratory Press, Cold Spring Harbor, N.Y., 1986); Westerfield, M., *The zebrafish book. A guide for the laboratory use of zebrafish* (*Danio rerio*), 4th Ed., (Univ. of Oregon Press, Eugene, Oreg., 2000).

EXAMPLES

The present invention can be described by reference to the following Examples, which are offered by way of illustration and are not intended to limit the invention in any manner. Standard techniques well known in the art or the techniques specifically described below were utilized.

Example 1

Testing Analogs

Analogs of RgIA were prepared using standard techniques well known in the art. These analogs were tested for activity on the α9α10 nAChR subtype using rat neuronal and human muscle nAChR subunits as previously described (Azam et al., 2005; Ellison et al., 2006; WO 2008/011006; US 2009/0203616). The analogs that were prepared and tested and the test results are shown in Table 1.

TABLE 1

Activity of Analogs

| Native Residue | Substituted Residue | SEQ ID NO: | $IC_{50}$ |
|---|---|---|---|
| RgIA | | | |
| Arg9 | no substitution | 1 | 3.2 nM |
| Arg9 | citrulline9 | 9 | 2.4 nM |
| Arg9 | ω-nitro-Arg9 | 10 | 2.3 nM |
| Arg9 | homo-Arg9 | 11 | >1 μM |
| Arg9 | ornithine9 | 12 | >1 μM |
| Arg9 | δ-N-acetyl-ornithine9 | 13 | >1 μM |
| Arg9 | Lys9 | 14 | >1 μM |
| Tyr10 | iodo-Tyr10 | 15 | 3.5 nM |
| Tyr10 | Trp10 | 16 | 11 nM |
| Tyr10 | Phe10 | 17 | 8.0 nM |
| Arg9, Tyr10 | citrulline9, iodo-Tyr10 | 18 | 1.1 nM |
| Arg9, Tyr10 | ω-nitro-Arg9, iodo-Tyr10 | 19 | 1.3 nM |
| Ser4 | Ala4 | 20 | 14.5 nM |
| Cys12Arg13 | Cys12-amide | 21 | 7.8 nM |
| Asp5 | Glu5 | 22 | 6.6 μM |
| Pro6 | Val6 | 23 | 4.1 μM |
| Arg9 | Ala9 | 24 | 13 μM |
| Asp5; Arg7 | His5; Ala7 | 25 | >10 μM |
| Arg9 | D-Arg | 26 | >3 μM |

The data presented in Table 1 suggests that $Arg_9$ in RgIA is essential for activity. The data further suggests that the nitrogen indicated by the arrow in Figure 6 is likely essential for activity (perhaps through hydrogen bonding). This was determined by substituting various non-standard amino acids for $Arg_9$. Finally, it is worth noting that the iodo-Tyr10, Arg9 Citrulline $IC_{50}$ is 1.1 nM and that the $IC_{50}$ for iodo-Tyr10, Arg9 omega-nitro-Arg is 1.3 nM. These analogs are more potent than the parent peptide. Although the differences are relatively small, a few fold difference can be very important from a cost of production standpoint.

Example 2

Testing Analogs

Analogs of RgIA were prepared using standard techniques well known in the art. Because it was found that RgIA is about 100-fold less potent on human α9α10 nAChR than on rat α9α10 nAChR, analogs were analyzed for potency on the human receptor. These analogs were tested for activity on the α9α10 nAChR subtype using human nAChR subunits as previously described (Azam et al., 2005; Ellison et al., 2006; WO 2008/011006; US 2009/0203616). The analogs that were prepared and tested and the test results are shown in Table 2.

TABLE 2

Activity of Analogs

| Analog[1] (SEQ ID NO:) | $IC_{50}$ on hα9α10 | 95% CI[2] |
|---|---|---|
| RgIA (1) | 854 nM | 619.4-1180 |
| RgIA[Y10Iodo] (41) | 107 nM | 75.6-152 |
| RgIA[Y10W] (16) | 268 nM | 163.5-438.4 |
| RgIA[S4T; R9Citr; Y10Iodo; R11Q] (27) | 18 nM | 13.6-23.6 |
| RgIA[R9Citr; Y10Iodo] (43) | 46 nM | 37.9-55.2 |
| RgIA[1-3sel; S4T; R9Citr; Y10Iodo; R11Q] (28) | 87 nM | 56-136 |
| RgIA[1-3sel; S4T; R9Citr; Y10Iodo; R11Q; R13L] (29) | 135 nM | 84.5-216.5 |
| RgIA[1-3sel] (30) | 242 nM | 165.5-354.7 |
| RgIA[R9Citr] (9) | 416 nM | 267.9-647 |
| RgIA[S4T; R9Citr; Y10Iodo] (31) | 109 nM | 79.4-150.7 |
| RgIA[S4T] (3) | 281 nM | 175-450 |
| RgIA[R11Q] (32) | 202 nM | 116-349 |
| RgIA[C2Homocysteine] (33) | >1000 nM | — |
| RgIA[S4A] (20) | >1000 nM | — |
| RgIA[S4Y] (34) | >1000 nM | — |
| RgIA[C8Homocysteine] (35) | >1000 nM | — |
| RgIA[R9Homoarginine] (11) | >1000 nM | — |
| RgIA[R9Ornithine] (12) | >1000 nM | — |
| RgIA[Y10F] (17) | >1000 nM | — |
| RgIA[R11H] (36) | >1000 nM | — |

[1]Citr = Citrulline; 1-3 sel = selenocysteine for 1st and 3rd cysteines; iodo = mono-iodo-Tyr;
[2]CI = Confidence Interval The data presented in Table 2 indicate that RgIA may be modified to substantially increase potency at the human α9α10 nAChR. Ser4, Arg9, Tyr10 and Arg11 may be individually modified such that the $IC_{50}$ is lowered (i.e. increased potency). In addition, the individually favorable modifications may be combined such that multiply substituted RgIA analogs have further increased in potency. For example, SEQ ID NO:27 for example is 47-fold more potent than the parent peptide. The results also indicate that selenocysteine may substitute for Cys; the resulting analogs containing a diselenide bond also show increased activity.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Arias, H. R. and Blanton, M. P. (2000). Alpha-conotoxins. *Int J Biochem Cell Biol* 32:1017-28.

Armishaw, C. J. and Alewood, P. F. (2005). Conotoxins as research tools and drug leads. *Curr Protein Pept Sci* 6:221-240.

Arredondo, J. et al. (2002). Central role of alpha7 nicotinic receptor in differentiation of the stratified squamous epithelium. *J Cell Biol* 159:325-336.

Azam, L. et al. Alpha-conotoxin BuIA, a novel peptide from *Conus bullatus*, distinguishes among neuronal nicotinic acetylcholine receptors. *J Biol Chem* 280:80-87 (2005).

Bennett, G. J. and Xie, Y. K. (1988). A peripheral mononeuropathy in rat that produces disorders of pain sensation like those seen in man. *Pain* 33:87-107.

Craik, D. J. et al. (2001). The cystine knot motif in toxins and implications for drug design. Toxicon 39:43-60.

Dutton, J. L. and Craik, D. J. (2001). α-Conotoxins: nicotinic acetylcholine receptor antagonists as pharmacological tools and potential drug leads. *Curr Med Chem* 8:327-344.

Elgoyhen, A. B. et al. (1994). α9: an acetylcholine receptor with novel pharmacological properties expressed in rat cochlear hair cells. *Cell* 79:705-715.

Elgoyhen, A. B. et al. (2001). α10: a determinant of nicotinic cholinergic receptor function in mammalian vestibular and cochlear mechanosensory hair cells. *Proc Natl Acad Sci USA* 98:3501-3506.

Ellison, M. et al. (2006). Alpha-RgIA: a novel conotoxin that specifically and potently blocks the alpha9alpha10 nAChR. *Biochemistry* 45:1511-1517.

Ettinger, L. J. et al. (1978). *Cancer* 41:1270-1273.

Gerzanich, V. et al., (1994). Homomers of α8 and α7 subunits of nicotinic acetylcholine receptors exhibit similar channel but contrasting binding site properties. *Mol. Pharmacol.* 45:212-220.

Gotti, C. and Clementi, F. (2004). Neuronal nicotinic receptors: from structure to pathology. *Prog Neurobiol* 74:363-396.

Haberberger, R. V. et al. (2004). Nicotinic acetylcholine receptor subtypes in nociceptive dorsal root ganglion neurons of the adult rat. *Auton Neurosci* 113:32-42.

Janes, R. W. (2005). alpha-Conotoxins as selective probes for nicotinic acetylcholine receptor subclasses. *Curr Opin Pharmacol* 5:280-292.

Karlin, A. (2002). Emerging structure of the nicotinic acetylcholine receptors. *Nat Rev Neurosci* 3:102-114.

Kurzen, H. et al. (2004). Phenotypical and molecular profiling of the extraneuronal cholinergic system of the skin. *J Invest Dermatol* 123:937-949.

Le Novere, N. et al. (2002). The diversity of subunit composition in nAChRs: evolutionary origins, physiologic and pharmacologic consequences. *J Neurobiol* 53:447-456.

Lee, C. H. et al. (2010a). Overexpression and activation of the alpha9-nicotinic receptor during tumorigenesis in human breast epithelial cells. *J Natl Cancer Inst* 102:1322-1335.

Lee, C. H. et al. (2010b). Crosstalk between nicotine and estrogen-induced estrogen receptor activation induces α9-nicotinic acetylcholine receptor expression in human breast cancer cells. *Breast Cancer Res Treat* 2010 Oct. 16. [Epub ahead of print].

Lewis, R. J. (2004). Conotoxins as selective inhibitors of neuronal ion channels, receptors and transporters. *IUBMB Life* 56:89-93.

Linnoila, R. I. (2010). From nicotine to breast cancer, implications of cholinergic receptor pathway. *J Natl Cancer Inst* 102:1298-1299.

Lips, K. S. et al. (2002). Coexpression of α9 and α10 nicotinic acetylcholine receptors in rat dorsal root ganglion neurons. *Neuroscience* 115:1-5.

Livett, B. G. et al. (2004). Drugs from the sea: conopeptides as potential therapeutics. *Curr Med Chem* 11:1715-1723.

Luer, M. S. and Hatton, J. (1993). *Annals Pharmcotherapy* 27:912-921.

McIntosh, J. M. et al. (1999). *Conus* peptides targeted to specific nicotinic acetylcholine receptor subtypes. *Annu Rev Biochem* 68:59-88.

McIntosh, J. M. et al. (2005). A novel α-conotoxin, PeIA, cloned from *Conus pergrandis*, discriminates between rat α9α10 and α7 nicotinic cholinergic receptors. *J Biol Chem* 280:30107-30112.

The Merck Manual of Diagnosis and Therapy, 17th Ed. (Merck & Co., Rahway, N.J., 1999).

Nguyen, V. T. et al. (2000). Novel human alpha9 acetylcholine receptor regulating keratinocyte adhesion is targeted by *Pemphigus vulgaris* autoimmunity. *Am J Pathol* 157:1377-1391.

Peng, H. et al. (2004). Characterization of the human nicotinic acetylcholine receptor subunit alpha (alpha) 9 (CHRNA9) and alpha (alpha) 10 (CHRNA10) in lymphocytes. *Life Sci* 76:263-280.

Remington: *The Science and Practice of Pharmacy*, 21st Ed., Lippincott Williams & Wilkins, Philadelphia, 2005.

Sgard, F. et al. (2002). A Novel Human Nicotinic Receptor Subunit, α10, That Confers Functionality to the α9-Subunit. *Mol Pharmacol* 61:150-159.

Terlau, H. and Olivera, B. M. (2004). *Conus* venoms: a rich source of novel ion channel-targeted peptides. *Physiol Rev* 84:41-68.

Vincler, M. et al. (2006). Molecular mechanism for analgesia involving specific antagonism of alpha9alpha10 nicotinic acetylcholine receptors. *Proc Natl Acad Sci USA* 103:17880-17884.

Wang, C. Z., and Chi, C. W. (2004). *Conus peptidessa* rich pharmaceutical treasure. *Acta Biochim Biophys Sin* 36:713-723.

Zimm, S. et al. (1984). *Cancer Res* 44:1698-1701.

---

What is claimed is:

1. An isolated conotoxin peptide having the formula X1GX2CX3DPRX4X5X6X7CX8X9 (SEQ ID NO:2), wherein:
   X1 is des-X1, pyroglutamic acid, Tyr, mono-halo-Tyr, or a fluorescent tag;
   X2 is Cys, selenocysteine (sel), or homocysteine;
   X3 is Ser, Thr, Ala, Tyr, halo-Tyr, Asn, Ile, or Arg;
   X4 is Cys or sel;
   X5 is Arg, citrulline, ω-nitro-Arg, homo-Arg, ornithine, or δ-N-acetyl-ornithine;
   X6 is Tyr, mono-halo-Tyr, Trp, or Phe;
   X7 is Arg, Gln, or His;
   X8 is Leu, Glu, Gln, or Lys; and
   X9 is des-X9, Tyr, mono-halo-Tyr, or a fluorescent tag; with the proviso that the conotoxin peptide of SEQ ID NO:2 is not a conotoxin peptide having the formula: GCCSDPRCRYRCK (SEQ ID NO:8).

2. A method of treating pain in an individual in need thereof, the method comprising administering to the individual a therapeutically effective amount of an active agent or a pharmaceutically acceptable salt thereof, the active agent comprising an isolated conotoxin peptide having the formula X1GX2CX3DPRX4X5X6X7CX8X9 (SEQ ID NO:2), wherein:
   X1 is des-X1, pyroglutamic acid, Tyr, mono-halo-Tyr, or a fluorescent tag;
   X2 is Cys, selenocysteine (sel), or homocysteine;
   X3 is Ser, Thr, Ala, Tyr, halo-Tyr, Asn, Ile, or Arg;
   X4 is Cys or sel;
   X5 is Arg, citrulline, ω-nitro-Arg, homo-Arg, ornithine, or δ-N-acetyl-ornithine;
   X6 is Tyr, mono-halo-Tyr, Trp, or Phe;
   X7 is Arg, Gln, or His;
   X8 is Leu, Glu, Gln, or Lys; and
   X9 is des-X9, Tyr, mono-halo-Tyr, or a fluorescent tag; with the proviso that the conotoxin peptide of SEQ ID NO:2 is not a conotoxin peptide having the formula: GCCSDPRCRYRCK (SEQ ID NO:8), thereby treating pain in the individual.

3. A method of treating inflammation mediated by immune cells in an individual in need thereof, the method comprising administering to the individual a therapeutically effective amount of an active agent or a pharmaceutically acceptable salt thereof, the active agent comprising an isolated conotoxin peptide having the formula X1GX2CX3DPRX4X5X6X7CX8X9 (SEQ ID NO:2), wherein:
   X1 is des-X1, pyroglutamic acid, Tyr, mono-halo-Tyr, or a fluorescent tag;
   X2 is Cys, selenocysteine (sel), or homocysteine;
   X3 is Ser, Thr, Ala, Tyr, halo-Tyr, Asn, Ile, or Arg;
   X4 is Cys or sel;
   X5 is Arg, citrulline, ω-nitro-Arg, homo-Arg, ornithine, or δ-N-acetyl-ornithine;
   X6 is Tyr, mono-halo-Tyr, Trp, or Phe;
   X7 is Arg, Gln, or His;
   X8 is Leu, Glu, Gln, or Lys; and
   X9 is des-X9, Tyr, mono-halo-Tyr, or a fluorescent tag; with the proviso that the conotoxin peptide of SEQ ID NO:2 is not a conotoxin peptide having the formula: GCCSDPRCRYRCK (SEQ ID NO:8), thereby treating inflammation mediated by immune cells in the individual.

* * * * *